United States Patent [19]
Crespo et al.

(10) Patent No.: US 7,543,472 B2
(45) Date of Patent: Jun. 9, 2009

(54) CALIBRATION ARRANGEMENT FOR BREATH TESTING EQUIPMENT

(76) Inventors: Pierre M. Crespo, 899 Williams Fork, Burkesville, KY (US) 42717; Michael Rader, 234 Hoffman Blvd., Ashland, PA (US) 17921

( * ) Notice: Subject to any disclaimer, the term of this patent is extended or adjusted under 35 U.S.C. 154(b) by 94 days.

(21) Appl. No.: 11/672,025

(22) Filed: Feb. 6, 2007

(65) Prior Publication Data

US 2007/0261468 A1  Nov. 15, 2007

Related U.S. Application Data

(60) Provisional application No. 60/765,631, filed on Feb. 6, 2006.

(51) Int. Cl.
*G01N 21/00* (2006.01)
(52) U.S. Cl. ...................................................... 73/1.06
(58) Field of Classification Search ............... 73/1.06, 73/1.02, 1.03; 422/84; 436/9
See application file for complete search history.

(56) References Cited

U.S. PATENT DOCUMENTS

| | | | |
|---|---|---|---|
| 3,521,045 A | 7/1970 | Murphy | 703/3 |
| 3,792,272 A | 2/1974 | Harte et al. | 250/343 |
| 3,842,345 A | 10/1974 | Padgitt et al. | 324/71.1 |
| 3,847,551 A | 11/1974 | Hutson | 436/9 |
| 3,853,477 A * | 12/1974 | Block et al. | 422/85 |
| 3,854,319 A | 12/1974 | Burroughs et al. | 73/1.03 |
| 3,948,604 A | 4/1976 | Hoppesch | 422/884 |
| 3,951,855 A | 4/1976 | Principe et al. | 436/9 |
| 4,090,078 A | 5/1978 | Heim | 250/343 |
| 4,132,109 A | 1/1979 | VanderSyde | 73/23.3 |
| 4,140,106 A | 2/1979 | Kirmaier | 600/532 |
| 4,163,383 A | 8/1979 | VanderSyde et al. | 73/23.3 |
| 4,266,751 A | 5/1981 | Akhavi | 251/6 |
| 4,292,978 A | 10/1981 | Guth | 600/543 |
| 4,300,385 A | 11/1981 | Albarda | 73/23.3 |
| 4,314,564 A | 2/1982 | Albarda | 600/532 |
| 4,353,869 A | 10/1982 | Guth | 422/102 |
| 4,363,635 A | 12/1982 | Hutson | 436/132 |
| RE31,246 E | 5/1983 | Adrian | 250/343 |
| 4,391,777 A | 7/1983 | Hutson | 422/84 |
| 4,407,152 A | 10/1983 | Guth | 73/1.03 |
| D272,559 S | 2/1984 | Guth | D24/110 |
| 4,459,994 A | 7/1984 | Slemeyer | 600/532 |
| 4,587,427 A | 5/1986 | Talbot et al. | 250/339.13 |
| D291,559 S | 8/1987 | Narveson | D13/199 |
| 5,134,875 A | 8/1992 | Jensen | 73/1.03 |
| 5,443,794 A | 8/1995 | Williams | 422/84 |
| 5,458,853 A | 10/1995 | Porter et al. | 422/84 |
| 5,493,891 A * | 2/1996 | Slemeyer | 73/1.06 |
| 5,552,324 A | 9/1996 | Liu | 436/132 |
| 5,834,626 A | 11/1998 | De Castro | 73/23.3 |
| 6,177,051 B1 | 1/2001 | Kimelman | 422/85 |
| 6,277,645 B1 | 8/2001 | Mault | 436/133 |

(Continued)

*Primary Examiner*—Hezron Williams
*Assistant Examiner*—Tamiko D Bellamy
(74) *Attorney, Agent, or Firm*—McNees Wallace & Nurick, LLC

(57) ABSTRACT

A calibration arrangement for breathalyzers wherein a heightened degree of control and management is applied. Broadly contemplated are arrangements whereby jars or containers of new solution to be used in the calibration arrangement are subject to automatic verification. Also contemplated is the close monitoring of the running of calibration tests and safeguards to ensure that extensively used or old solution is not put into use.

27 Claims, 3 Drawing Sheets

U.S. PATENT DOCUMENTS

| | | | |
|---|---|---|---|
| 6,464,941 B1 | 10/2002 | Diekmann | 422/84 |
| 6,526,802 B1 | 3/2003 | Fisher | 73/1.03 |
| 7,403,873 B2 | 7/2008 | Okuno et al. | 702/187 |
| 7,404,311 B2 | 7/2008 | Guth et al. | 73/1.03 |
| 2003/0216660 A1* | 11/2003 | Ben-Oren et al. | 600/532 |
| 2004/0019460 A1* | 1/2004 | Okuno et al. | 702/187 |
| 2005/0009195 A1 | 1/2005 | Wang | 436/84 |
| 2005/0083527 A1* | 4/2005 | Flaherty et al. | 356/437 |
| 2005/0135969 A1 | 6/2005 | Olsson et al. | 422/84 |
| 2005/0214169 A1 | 9/2005 | Leddy | 422/84 |
| 2008/0046503 A1 | 2/2008 | Okuno et al. | |

* cited by examiner

SAMPLE PARTIAL SMARTSIM DATALOGGER

```
SMARTTECH, INC.
SMARTSIM™ DATALOGGER

SMARTSIM™ LOCATION:
ASHLAND POLICE DEPARTMENT
426 WALNUT STREET
ASHLAND, PA  17921
PHONE: 570-555-5555

EVENT LOG DATA
DATE RANGE
01/01/05-04/01/05

01/01/05   12:00PM    SMARTSIM POWER ON
           12:00PM    TEST COUNTER RECORD (0)
           12:00PM    TIME COUNTER RECORD (0)
           12:00PM    SCAN TECH ID BAR-CODE PROMPT
           12:01PM    TECH ID BAR-CODE SCANNED: ACCEPTED
           12:01PM    TECH ID INFORMATION:
                      TECH NAME: MICHAEL RADER
                      DEPARTMENT: ASHLAND POLICE DEPARTMENT
                      BADGE NUMBER: 837495
                      ADDRESS: 426 WALNUT STREET, ASHLAND, PA 17921
           12:02PM    SCAN SOLUTION BAR-CODE PROMPT
           12:03PM    SO.UTION BAR-CODE SCANNED: ACCEPTED
           12:03PM    SOLUTION INFORMATION:
                      MANUFACTURE DATE: 10/01/04
                      EXPIRATION DATE: 10/01/05
                      ALCOHOL CONCENTRATION: .10%
                      LOT NUMBER: 856
                      LOT VOLUME: 50 GALLONS
                      LOT BOTTLE NUMBER: 945
                      SMARTTECH BOTTLE NUMBER: 000000000001
                      SOLUTION APPROVING LABORATORY:
                      SMARTTECH, INC.
                      234 HOFFMAN BLVD
                      ASHLAND, PA 17921
                      PHONE: 717-610-0273
           12:04PM    FILL SMARTSIM PROMPT
           12:06PM    SMARTSIM FILLED
                      VOLUME: 500ML
           12:06PM    TEST COUNTER RESET (0)
           12:06PM    TIME COUNTER RESET (0)
           12:07PM    RUN MODE ENABLE
           12:07PM    TEMPERATURE 25°C
           12:07PM    HEATER ON
           12:07PM    AGITATIOR ON
           12:07PM    TEMPERATURE SENSOR ON
```

FIG. 3

CALIBRATION ARRANGEMENT FOR BREATH TESTING EQUIPMENT

CROSS-REFERENCE TO RELATED APPLICATION

This application claims the benefit of U.S. Provisional Patent Application Ser. No. 60/765,631, filed on Feb. 6, 2006, and which is fully incorporated by reference herein.

FIELD OF THE INVENTION

The present invention relates to alcohol detection equipment, such as in the context of breath testing in DUI enforcement. Particularly, the present invention relates to the calibration of breath testing equipment.

BACKGROUND OF THE INVENTION

Breath testing equipment, or "breathalyzers", are very widely known. Air from an individual is typically passed through a breathalyzer to determine the percentage alcohol content. However, problems have long been presented in terms of the accuracy of such equipment, meaning that proper calibration is extremely vital. In the absence of properly calibrated breathalyzer equipment, the validity and reliability of any associated breath tests will come into question and may present difficulties in terms of adequately "making a case" in a court of law This is where calibration arrangements, often known as "simulators", play a role. These arrangements will accommodate a given breathalyzer for testing, and a sample will normally be used that is not from human breath. For the latter purpose, a solution with a known alcohol concentration is typically used.

Calibration arrangements have been developed over the years, but still tend not to be as reliable as might be desired in many settings. For instance, a perennial problem is encountered in connection with the re-use of a single jar or container of alcohol solution; since the alcohol percentage in the solution will change over time, it eventually becomes unreliable. Accordingly, a need has been recognized in connection with providing an even more reliable calibration arrangement for breath testing equipment than has hitherto been the norm.

The present invention puts some controls on the calibrations (or simulations). Think of the solution in the calibrator (or simulator) as the reference standard to which all other breathalyzers are compared; if your standard if off, so is everything else.

SUMMARY OF THE INVENTION

Broadly contemplated herein, in accordance with at least one presently preferred embodiment of the present invention, is a calibration arrangement for breathalyzers wherein a heightened degree of control and management is applied.

In summary, one aspect of the invention provides an apparatus for calibrating breath analyzing equipment, the apparatus comprising: an operator interface which apprises an operator of at least one condition of the apparatus; a data input arrangement which accepts data regarding at least one of: the operator and a solution for simulating alcoholized breath; a receiving portion which is adapted to receive new solution for simulating alcoholized breath; and an arrangement for preventing usage of solution beyond at least one predetermined threshold parameter.

Furthermore, an additional aspect of the invention provides a method of calibrating breath analyzing equipment, the method comprising the steps of: apprising an operator of at least one condition; accepting data regarding at least one of: the operator and a solution for simulating alcoholized breath; receiving new solution for simulating alcoholized breath; and preventing usage of solution beyond at least one predetermined threshold parameter.

BRIEF DESCRIPTION OF THE DRAWINGS

The above and other objects, features, and advantages of the present invention will become more apparent from the following detailed description when taken in conjunction with the accompanying drawings, in which:

FIG. 3 provides a sample datalogger report.

DETAILED DESCRIPTION OF THE INVENTION

Figure 1:
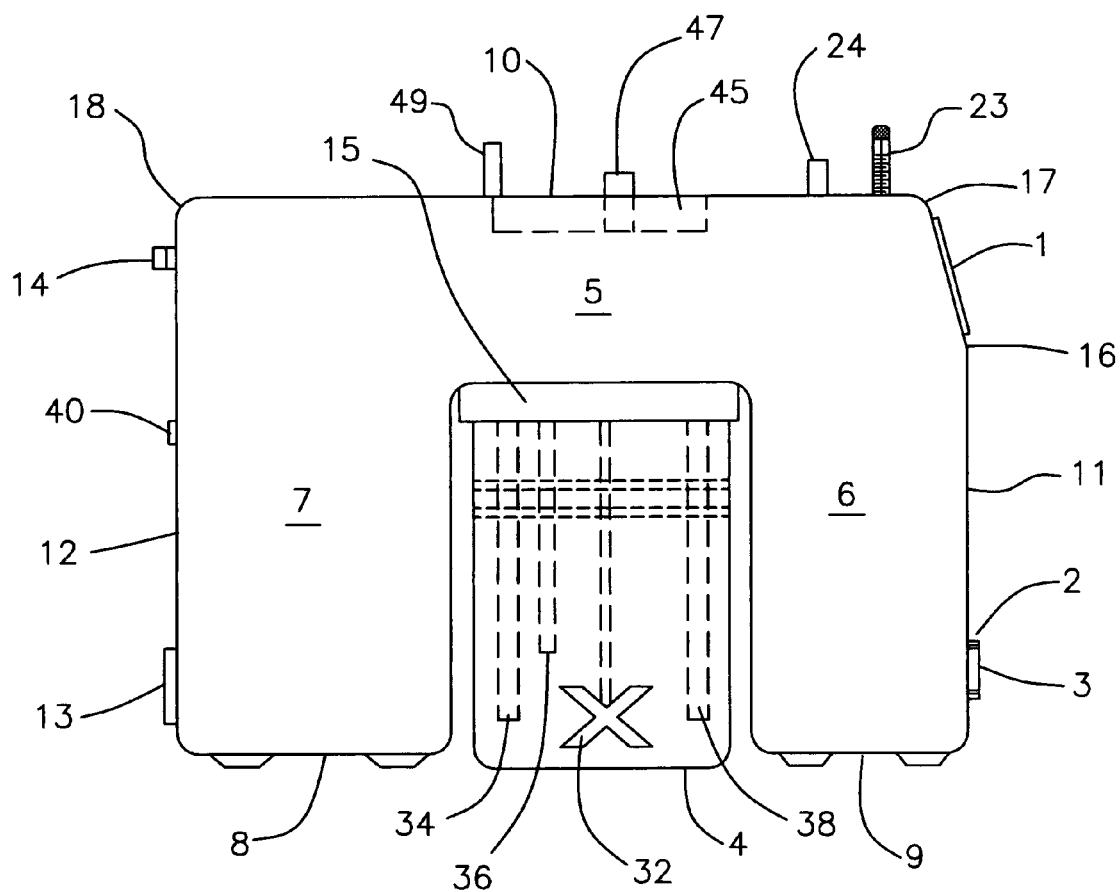
FIG. 1 illustrates a first elevational view of a breath detection apparatus.
Figure 2:
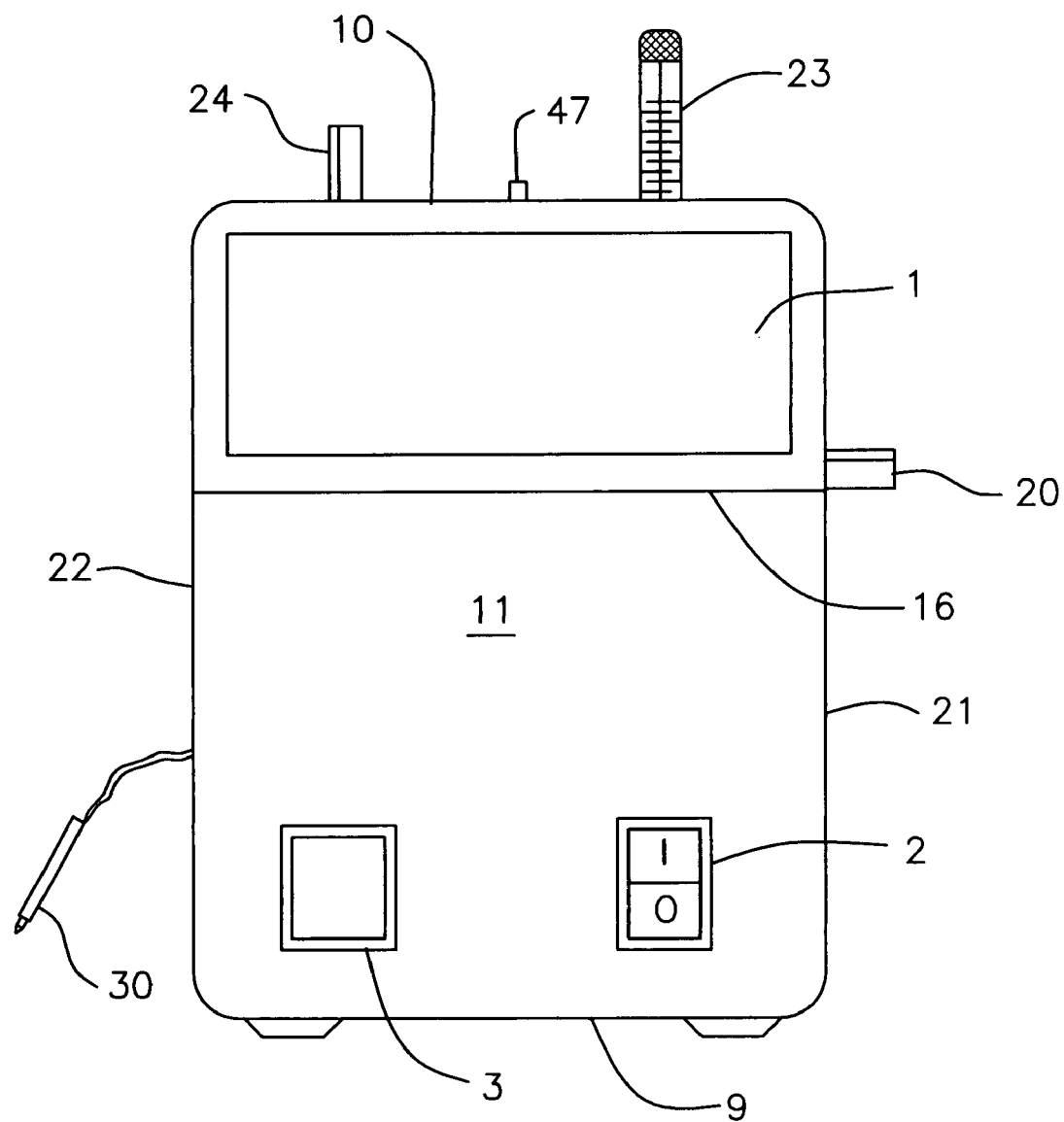
FIG. 2 illustrates a second elevational view of a breath detection apparatus.

FIGS. 1 and 2 respectively illustrate first and second elevational views, orthogonally distinct from one another, of a calibration apparatus in accordance with a preferred embodiment of the present invention. In the discussion herebelow, reference may be made to both figures simultaneously.

The calibration apparatus (alternatively termed a "simulator" or "unit" herein) includes a top portion 10, rear portion 12 and front portion 11. At the front portion 11, edges 16 and 17, as shown, preferably define an angled portion which accommodates a GUI (or graphical user interface) touch screen display 1. (Other corners and edges such as that indicated at 18 are preferably rounded as shown.) In terms of basic functional components, a power switch 2 is configured for activating the unit while a pump switch 3 is configured for receiving an input of air from a non-human sample. A power inlet 13 may be provided at rear portion 12, along with a heated tube plug-in 14.

The "left" side of the unit (with respect to display 1) includes a top portion 5, left and right portions 7 and 6 (respectively) and bottom portions 8 and 9 (respectively). Portions 7/8 and 6/9, as shown, are preferably configured to flank a space sufficient for accommodating a solution container (e.g., and most preferably, a 500 ml glass jar or container) 4, while top portion 5 provides sufficient clearance therefor. A threaded connection or collar 15 on the unit is preferably provided for securely accommodating jar or container 4. Though normally this jar/container 4 will serve as a receptacle for solution that is introduced from above, it should be appreciated that the connection/collar 15 will ensure that it can be removed, as needed, for replacement, or simply for "dumping" out old solution.

The unit preferably further includes a vapor output tube 20 which, e.g., may extend from a "right" side of the unit. Atop the unit, as shown, there are also preferably provided an air-in tube 24 and, optionally, a thermometer 23 (such as an NIST [National Institute of Standards and Technology] approved thermometer). Tubes 20 and 24, and thermometer 23, preferably function in similar manner to known calibration units and thus will not be discussed in significant detail herein; essentially incoming air is exposed to solution in jar/container 4, and outgoing "vapor", simulating human breath, will proceed to a breathalyzer that is being calibrated.

For the purposes of scanning in various types of information (as discussed below), such as from barcodes, essentially any suitable input arrangement can be provided. For example, a conventional barcode scanning reader, as indicated at 30 (albeit not to scale), may be provided. (Alternatives to an integral barcode reader are of course possible, such as a "pen" barcode reader or even a magnetic stripe reader.

The functioning of a unit as just described will now be better appreciated from the discussion below, as will components that have not yet been specifically mentioned.

Preferably, a unit in accordance with the present invention will offer at least two operating choices, "systems on" and "run". Thus, on/off switch 2 will power up the unit to enable access to menu options and add or change solution (as described below). On the other hand, the pump switch 3 will put the unit in full operating mode, as will be appreciated below.

Preferably, in "systems on", the operator will be prompted to provide or scan in a "tech ID" (e.g., from a barcode on a card or badge). This will draw on operation information contained in a database or other data storage (such as in a datalogger internal to the unit), and operator information will be displayed on screen 1, as well as be recorded for a "report" (see further below). "Test counter" and "day counter" records will then be consulted to determine if the corresponding counters have exceeded predetermined values set for the solution within the unit (i.e., within jar/container 4). In other words, if a given solution (in container 4) has been used for at least one "too many" tests or at least one "too many" days, the "run" mode will be disabled and the operator will be prompted (e.g. via a message on screen 1) to change the alcohol solution.

At that point (assuming a new container is needed), the operator will preferably be prompted to scan—e.g., via a conventional reader 30 at right side 21—both the "tech ID" and an identifier for the new container (such as a barcode on the container), whereupon the following will now preferably be displayed on screen 1 and recorded: complete "tech ID" information and the date that the solution was scanned. Once the alcohol solution has been changed (per below), the "test counter" and "day counter" parameters will revert to zero.

Preferably, once the bar code or other identifier of the solution has been scanned, a provision will ensure that the same container cannot be scanned in again. If the same container is scanned twice, preferably it will be displayed and recorded that the container has already been scanned and that the solution involved may not be used again. Then, "run" mode preferably will not be enabled until an acceptable "tech ID" and new solution bar code or identifier have been received or scanned.

It should be understood that if, during this scanning process, the upper limits for "test counter" and "day counter" have not been exceeded, then there is no need to scan in a new bottle or container before performing a calibration test. Solution container 4 will thus already contain solution that can be used.

As such, solution container 4, as shown, is preferably a "receptacle" for holding existing solution or accepting new solution. After solution contained therein has exceeded its useful life (e.g., with the "test counter" and/or "day counter" parameters being exceeded), the solution is preferably drained in preparation for the introduction of new solution, as discussed below Indicated at 45 in FIG. 1 is a region where a fresh solution jar or container. can be introduced, in accordance with a preferred embodiment of the present invention. Preferably, region 45 will be embodied by a depression or recession, e.g. of generally circular cross-sectional shape, for accepting an overturned solution jar or container. Preferably protruding from region 45 is a male inlet port 47 for accepting fresh solution.

As such, inlet port 47 could initially be protected by a sealing cap or other suitable protection arrangement. A new jar/container of fresh solution, if needed, and after having been "scanned in" as described above, will itself preferably contain a female port, e.g., initially sealed off w/a pierceable membrane or cap. By inverting the new jar/container onto the inlet port 47, a fluid connection will thus initiate between the new jar/container and inlet port 47. Though not shown, a suitable internal fluid conduit will then preferably direct this new solution downwards into jar/container 4, now acting as a "receptacle". (It should be clearly understood that ahead of time the jar/container 4 will have been drained or emptied, e.g., by removing the jar and dumping out the contents or via a drain valve or the like at the bottom of jar/container 4.)

Preferably also included is a data coupling 49, configured for integrating with a mating data port on the new jar/container, for receiving information from the jar/container such as: the solution's manufacturing date, its expiration date, alcohol concentration, lot number, lot volume, bottle number from the lot, and a laboratory that may have approved the solution. A unique identifier such as an overall "bottle number" (as opposed to a bottle number from a lot) could also be included in this information. This might help ensure that only "authorized" bottles are being used. Preferably, the mating data port on the jar/container being introduced will be in communication with a RFID tag or the like on (or associated with) the jar/container, on which the aforementioned information is stored and from which can then progress through to the coupling 49. As one example, an RFID tag can be attached to or at a cap portion of the "incoming" jar/container. Such an arrangement is available from Colder Products, Inc., of St. Paul, Minn. Of course, this is but one example of an arrangement via which information regarding a jar/container of solution can be made available to a simulator. As such, such information could conceivably—alternatively or in addition—be availed through barcode reader 30 or analogous device (e.g., a magnetic stripe reader which reads a magnetic stripe on the incoming jar/container or on a card associated with the incoming jar/container).

With the jar/container 4 newly filled, the operator can replace a sealing cap (if any) on inlet port 47. The "run" mode may now be initiated.

It should be understood, again, that a test may be immediately run, and many of the above steps bypassed, if the solution in jar/container 4 is not yet "old" and thus does not need to be dumped. However, a suitable sensor will preferably be configured for detecting when the jar/container 4 is indeed removed from connector 15 (ostensibly for dumping). Preferably, to ensure the functionality and accuracy of the device, if jar/container 4 is removed for any reason between solution changes, the operator will dump the entire solution. The sensor, in this case, would thus preferably relay a prompt to produce a message on screen 1 (or through some other means) to the effect that the solution must be dumped, whereby "run" mode will be temporarily disabled.

Among the standard components preferably extending into jar/container 4 are an agitator 32, temperature sensor 34, heater 36 and liquid sensor 38. These all preferably function in a manner well-known to those of ordinary skill in the art, and thus will not be further described herein. These four components (32/34/36/38) are preferably disabled whenever "run" mode is deactivated or disabled.

The "test counter" described hereabove may be embodied by essentially any suitable means, including an internal flow meter which is configured for counting the number of tests run, until new solution is introduced. Optionally, there may be an internal air input pump whereby the "test counter" would sense voltage and thus make a count based on an air pump trigger. If "too many" tests have been run, an operator prompt will preferably be provided as discussed heretofore.

The "day counter" described hereabove will preferably be configured to disable "run" mode, and thus components 32/34/36/38, after a predetermined number of days (such as 45), while providing an operator prompt as discussed heretofore.

In accordance with a variant refinement of the present invention, the operator could be queried (e.g. via screen 1) as to whether he/she wants to scan his/her "tech ID" at those times when a test is being run but solution is not being changed. Via a touch screen or button, "yes" could be selected if he/she wishes to scan in the ID, and "no" if not. Either way, the test may proceed but the fact that the operator did or didn't scan in could be recorded in the datalogger. Of course, preferably, the operator will always be prompted to scan in the "tech ID" when solution is being changed.

In accordance with another variant refinement of the present invention, a "maintenance mode" can engage after a given number of tests (which may or may not coincide with the upper limit defined by the "test counter") or a predetermined time frame (which may or may not coincide with the upper limit defined by the "day counter"). Preferably, when a "maintenance" prompt is activated, the operator will be directed to insert into recession/depression 47 not a jar/container of solution but a jar/container of cleaning fluid, followed by a jar/container of rinse fluid. (Or, rather than the use of jars/containers for these purposes, it is conceivable to successively connect one or more fluid connections, such as a tube or hose for each of the cleaning fluid and rinsing solution, to inlet port 47, or to connect just one such tube/hose which could by itself successively admit cleaning fluid then rinsing solution.) As can be appreciated, jars/containers of cleaning fluid and rinsing solution can preferably be "scanned" in similarly to the jars/containers of solution described above.

A data port 40 (such as an RS232) may preferably be provided at a rear of the unit, as shown, for uploading internal data to an external source such as a PC. For instance, when the internal memory (essentially constituted by the datalogger) nears capacity, a prompt could be provided (e.g. via screen 1) to upload the data. Suitable software on the PC may preferably be specifically configured for this purpose. At the same time, port 40 can also be configured for downloading into the unit any suitable external data, such as product software updates. Data uploaded to a PC can of course be stored and printed locally for record keeping and future reference. Alternatively, a print port could be provided on the unit via which to directly export data from the unit's internal datalogger to a printer.

As such, preferably, a bar code can be put on each evidentiary breath tester or breathalyzer that the unit is involved in calibrating. The bar code can be scanned with reader 30 and thereby inputted into the datalogger. A record can then be produced to the effect that a given breathalyzer was indeed calibrated at a certain time and date with a certain solution, that itself has been shown to be reliable within a given time window and given number of tests.

FIG. 3 shows a sample datalogger report that could be generated and produced in accordance with the process steps described hereinabove. The recorded steps shown progress as far as enabling "run" mode, subsequent to verifying that an acceptable bottle of solution has been used to fill jar/container 4.

If not otherwise stated herein, it is to be assumed that all patents, patent applications, patent publications and other publications (including web-based publications) mentioned and cited herein are hereby fully incorporated by reference herein as if set forth in their entirety herein.

Although illustrative embodiments of the present invention have been described herein with reference to the accompanying drawings, it is to be understood that the invention is not limited to those precise embodiments, and that various other changes and modifications may be affected therein by one skilled in the art without departing from the scope or spirit of the invention.

What is claimed is:

1. An apparatus for calibrating breath analyzing equipment, said apparatus comprising:
   a screen display which displays at least one condition of said apparatus;
   data storage for storing data;
   a database that includes operator information stored in the data storage;
   a first data input arrangement which identifies an operator, recalls operator data from the database and displays operator data on the screen display;
   a second data input arrangement that identifies a solution for simulating alcoholized breath and stores data about the solution in the data storage and displays solution data on the screen display;
   a receiving portion which is adapted to receive the solution for simulating alcoholized breath;
   means for identifying the date the solution was added to the receiving portion, storing the date in the data storage with the solution data; and
   an arrangement for analyzing stored solution data that disables the apparatus when at least one predetermined threshold parameter of the solution is exceeded and prompts the operator to change the solution.

2. The apparatus according to claim 1, wherein the at least one predetermined threshold parameter comprises at least one of: a time parameter and a usage parameter, and displaying the at least one threshold parameter on the screen display.

3. The apparatus according to claim 2, wherein the time parameter is determined from the date stored in the database with the solution data.

4. The apparatus according to claim 2, wherein the usage parameter relates to a number of uses of the solution stored in the database with the solution data.

5. The apparatus according to claim 1, further comprising a single, undivided receptacle for holding solution for simulating alcoholized breath.

6. The apparatus according to claim 5, wherein:
   the arrangement for analyzing stored solution data comprises analyzing data for at least the following conditions of the solution:
      the date the solution was added to the receiving portion and storing data regarding the date the solution was added; and
      a run condition, indicative of the number of times during which the solution in the receptacle is employed in calibrating breath analyzing equipment and storing the data indicative of the number of times the solution is employed; and the arrangement for analyzing stored solution data is configured for disabling the run condition of the apparatus responsive to exceeding the at least one predetermined threshold parameter.

7. The apparatus according to claim 1, further comprising at least one physical port for interfacing with a breathalyzer.

8. The apparatus according to claim 1, wherein said data input arrangement comprises a barcode reader for providing identifying data regarding at least one of the operator data and the solution.

9. The apparatus according to claim 1, wherein said receiving portion further comprises at least one port for interfacing with a provision medium of solution.

10. The apparatus according to claim 9, wherein said at least one port further comprises an arrangement for automatically receiving data regarding a provision medium of solution as a provision medium of solution interfaces with at least one port, storing the data in data storage and displaying the data on the screen display.

11. The apparatus according to claim 10, wherein the at least one port further comprises a second fluid inlet port for receiving solution from a provision medium of solution.

12. A method of calibrating breath analyzing equipment, said method comprising the steps of:
inputting data into a database that includes operator information stored in a data storage;
inputting data identifying a solution;
inputting data identifying a date the solution was added to a receiving portion of apparatus for calibrating breath analyzing equipment and storing the data in data storage;
providing a screen display in communication with the data storage;
displaying operator data recalled from data storage on the screen display;
displaying solution data recalled from data storage on the screen display; and
preventing usage of solution beyond at least one predetermined threshold parameter.

13. The method according to claim 12, where the at least one predetermined threshold parameter comprises a time parameter determined from data in data storage identifying the date the solution was added to the apparatus.

14. The method according to claim 12 wherein the at least one predetermined threshold parameter includes a usage parameter regarding the number of uses of the solution, the number of uses stored in the database with the solution data.

15. The method according to claim 12, wherein:
said step of preventing usage further comprises affording at least the following conditions:
a start condition, during which data is input regarding the identity of the operator, compared with operator data in data storage and displayed on the screen display, and data regarding the solution is and data regarding the solution is displayed on the screen display; and
a run condition, during which The given solution is employed; and
said step of preventing usage comprises disabling the apparatus to prevent execution of the run condition responsive to breaching of the at least one predetermined threshold parameter.

16. The method according to claim 15, further including a step of receiving data regarding the solution, and storing the data in data storage.

17. The apparatus of claim 1 wherein the screen display includes a graphical user interface touch screen display.

18. the apparatus of claim 1 wherein the apparatus includes a print port.

19. The method of claim 12 wherein the steps of displaying data on the screen display includes displaying data on a graphical user interface touch screen display.

20. The method of claim 12 further including the step of exporting data from the database.

21. The method of claim 20 wherein the data is exported to a printer and the data is printed.

22. The method of claim 12 wherein the data identifying the solution identifies data selected from at least one category in the group consisting of a unique identifier, a manufacturing date, an expiration date, an alcohol concentration, a lot number, a lot volume and an approving laboratory.

23. The method of claim 22 wherein the unique identifier is a lot.

24. The method of claim 22 further including a bottle number from the numbered lot.

25. The method of claim 12 further including the additional steps of counting the number of times a calibration test has been run using the solution.

26. The method of claim 12 further including the step of inputting data into the database that identifies an evidentiary breath tester that is calibrated using the solution.

27. The method of claim 26 further including inputting into the database the time and date that an evidentiary breath tester is calibrated using the solution.

* * * * *